(12) United States Patent
Ohishi

(10) Patent No.: US 12,042,673 B2
(45) Date of Patent: Jul. 23, 2024

(54) RADIATION THERAPY APPARATUS AND RADIATION THERAPY METHOD

(71) Applicant: CANON MEDICAL SYSTEMS CORPORATION, Tochigi (JP)

(72) Inventor: Satoru Ohishi, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 204 days.

(21) Appl. No.: 17/509,476

(22) Filed: Oct. 25, 2021

(65) Prior Publication Data

US 2022/0126119 A1 Apr. 28, 2022

(30) Foreign Application Priority Data

Oct. 26, 2020 (JP) .................................. 2020-178651

(51) Int. Cl.
*A61N 5/10* (2006.01)
(52) U.S. Cl.
CPC ......... *A61N 5/1081* (2013.01); *A61N 5/1031* (2013.01); *A61N 5/1048* (2013.01)
(58) Field of Classification Search
None
See application file for complete search history.

(56) References Cited

U.S. PATENT DOCUMENTS

| 6,385,288 | B1 | 5/2002 | Kanematsu | |
| 2004/0254773 | A1* | 12/2004 | Zhang | A61B 6/541 |
| | | | | 703/11 |
| 2019/0336795 | A1* | 11/2019 | Zhou | A61N 5/1081 |
| 2021/0370097 | A1* | 12/2021 | Thomas | A61N 5/1068 |
| 2022/0008751 | A1* | 1/2022 | Sadeghi | A61N 5/1049 |

FOREIGN PATENT DOCUMENTS

JP 2002-210029 A 7/2002

OTHER PUBLICATIONS

Edvardsson et al., "Motion Induced Interplay Effects for VMAT Radiotherapy" Institute of Physics and Engineering in Medicine, Phys. Med. Biol. 63, Apr. 19, 2018, 15 pages.

* cited by examiner

*Primary Examiner* — Hoon K Song
(74) *Attorney, Agent, or Firm* — Oblon, McClelland, Maier & Neustadt, L.L.P.

(57) ABSTRACT

A radiation therapy apparatus of an embodiment allows radiation to be applied while rotating a gantry and controls irradiation and stop of the radiation during the rotation of the gantry based on respiration of a treatment subject, and includes processing circuitry. The processing circuitry detects the respiration of the treatment subject. The processing circuitry predicts an administration dose based on a respiratory phase range in which the radiation is applied in the respiration of the treatment subject, and changes at least one or both of a dose rate of the radiation to be applied to the treatment subject and a rotation speed of the gantry so that the administration dose reaches a target dose. The processing circuitry performs control according to the change with respect to at least one or both of the dose rate of the radiation and the rotation speed of the gantry.

14 Claims, 8 Drawing Sheets

FIG.7
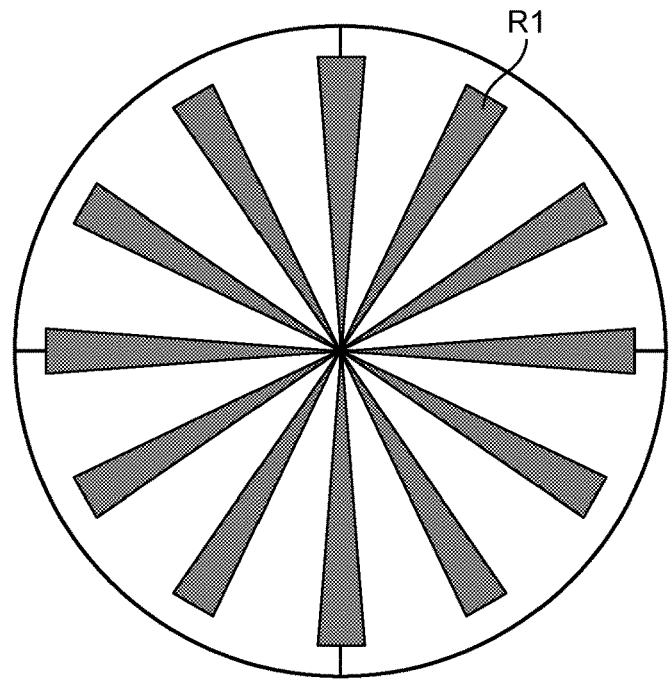
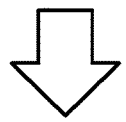
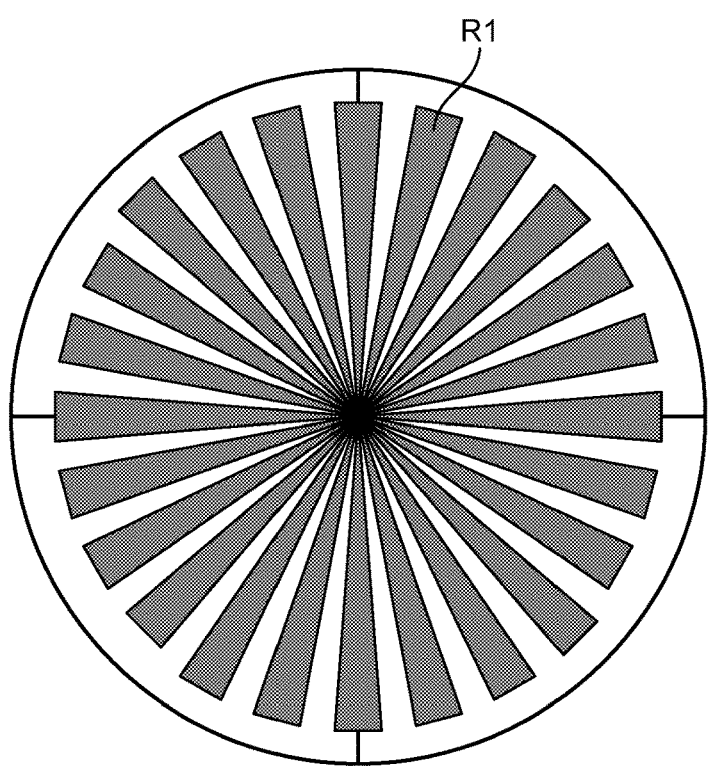

FIG.9
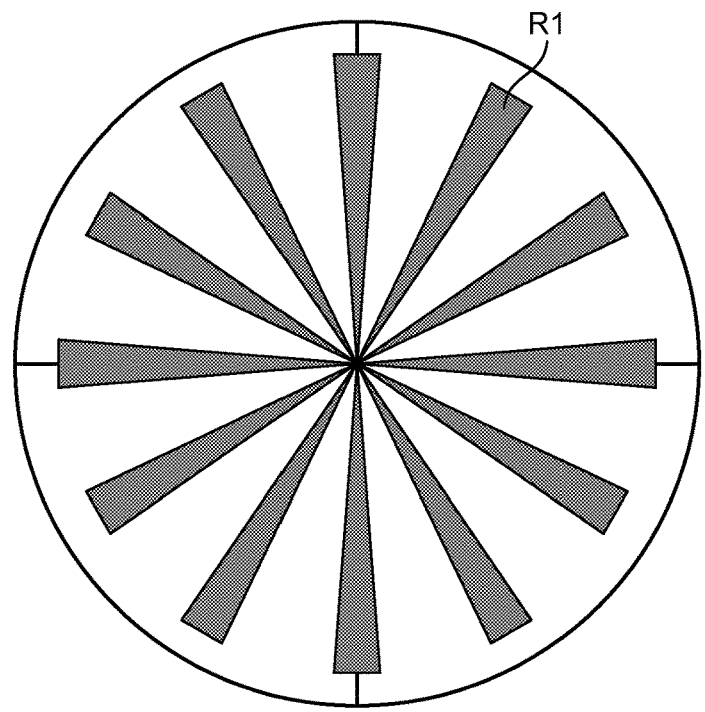
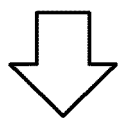
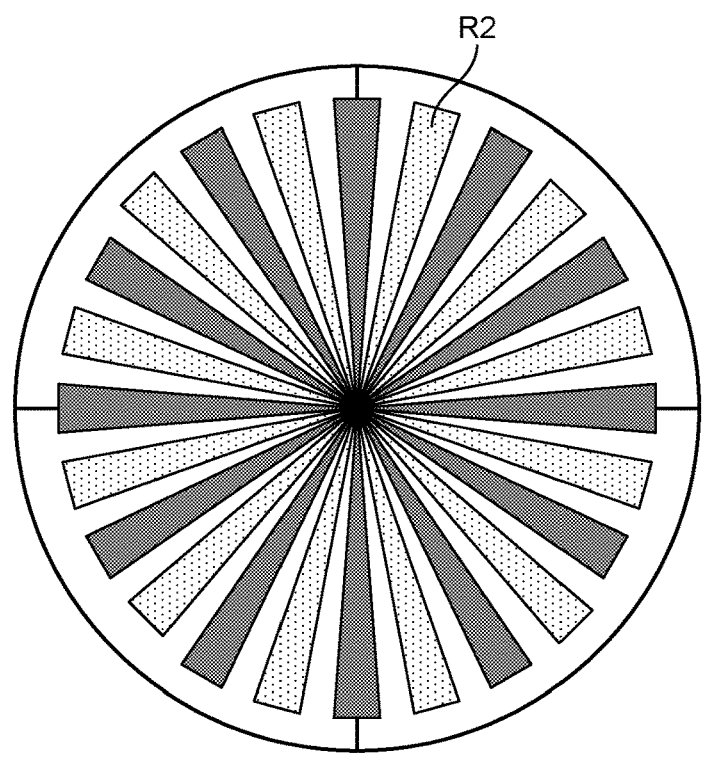

RADIATION THERAPY APPARATUS AND RADIATION THERAPY METHOD

CROSS-REFERENCE TO RELATED APPLICATIONS

This application is based upon and claims the benefit of priority from Japanese Patent Application No. 2020-178651, filed on Oct. 26, 2020; the entire contents of which are incorporated herein by reference.

FIELD

Embodiments described herein relate generally to a radiation therapy apparatus and a radiation therapy method.

BACKGROUND

The mainstream of radiation therapy is intensity modulated radiation therapy (IMRT) or intensity modulated particle therapy (IMPT) in which intensity modulated X-rays or particle beams are emitted from a plurality of directions. However, these methods have problems such as a need to confirm a patient's position each time the irradiation direction is changed, and increased radiation exposure to a normal tissue in front of a tumor in the irradiation direction.

On the other hand, in recent years, a method in which X-rays or particle beams are emitted while rotating a gantry has been adopted. The method in which X-rays or particle beams are emitted while rotating a gantry is called a volumetric modulated arc therapy (VMAT) and a particle arc therapy. These methods have advantages such as 1) high throughput (the number of times to check patient's position is only one in the case of, for example, a single rotation irradiation), 2) small radiation exposure to a normal tissue in front of a tumor in the irradiation direction, and 3) simple treatment planning (because there is no need to select an irradiation angle).

The VMAT or the particle arc therapy can significantly improve throughput from treatment planning to treatment (patient alignment and beam irradiation). Therefore, when a super-aging society arrives in the near future, it is expected that the VMAT or the particle arc therapy will play a central role in radiation therapy.

The VMAT or the particle arc therapy has many advantages as described above, but caution is required in organs (lung, liver, and the like) with a respiratory motion. For example, known as treatment of organs with a respiratory motion include: 1) continuous irradiation during respiration (wide irradiation of range of motion by respiration+margin), 2) breath-hold irradiation, 3) suppression of a respiratory motion (suppression of a respiratory motion by tightening abdomen with a band and the like), 4) gate irradiation (perform irradiation only when respiration is in a desired phase), 5) tracking irradiation (monitoring of changes in a tumor position and irradiation according to the tumor position), and the like. However, in 1), radiation exposure to a normal tissue is increased. In 2), even a healthy person can hold his/her breath stably for only about 15 seconds; thus, it is even shorter in a target patient, and breath holding during irradiation is very difficult. In 3), a burden on a patient is heavy and the respiratory motion may not be suppressed depending on a patient. In 5), since a cancer itself is not seen, the cancer can only be estimated on the basis of the movement of nearby organs or a marker can only be inserted near the cancer tissue. However, the former has the problem that the movement of the organs and the movement of the tumor are not always correlated with each other, and the latter has a trouble of inserting the marker and a risk of marker separation. From these facts, in the treatment of organs with a respiratory motion, all in all, 4) gate irradiation can be stably performed in the treatment of organs with a respiratory motion.

In the VMAT or the particle arc therapy, roughly two types of gate irradiation method exist. One method is to rotate a gantry only during an irradiation period, and the other method is to rotate the gantry not only during the irradiation period, but also during an irradiation pause period between the adjacent irradiation periods. In the former method, the rotation speed needs to slow down significantly, and the gantry needs to stop immediately when the pause period is reached. One problem with this method is that, since the rotation speed is low, one rotation takes time. Moreover, if the gantry fails to stop at the beginning of the pause period, it may overrun, and thus the angle of the overrun needs to be returned by reversely rotating the gantry.

BRIEF DESCRIPTION OF THE DRAWINGS

FIG. 7 is a diagram illustrating irradiation angles of radiation applied by the radiation therapy apparatus according to the second embodiment;

FIG. 9 is a diagram illustrating irradiation angles of radiation applied by the radiation therapy apparatus according to a third embodiment.

DETAILED DESCRIPTION

A radiation therapy apparatus of an embodiment is a radiation therapy apparatus that allows radiation to be applied while rotating a gantry and controls irradiation and stop of the radiation during the rotation of the gantry on the basis of the respiration of a treatment subject, and includes processing circuitry. The processing circuitry detects respiration of the treatment subject. The processing circuitry predicts an administration dose on the basis of a respiratory phase range in which the radiation is applied in the respiration of the treatment subject, and changes at least one or both of a dose rate of the radiation to be applied to the treatment subject and a rotation speed of the gantry so that the administration dose reaches a target dose. The processing circuitry performs control according to the change with respect to at least one or both of the dose rate of the radiation and the rotation speed of the gantry.

Hereinafter, embodiments of a radiation therapy apparatus and a radiation therapy method according to the present application will be described in detail with reference to the accompanying drawings. Note that the radiation therapy apparatus and the radiation therapy method according to the present application are not limited to embodiments to be described below. Furthermore, the embodiments can be combined with other embodiments or the related arts as long as no contradiction occurs in processing content.

First Embodiment

Figure 1:
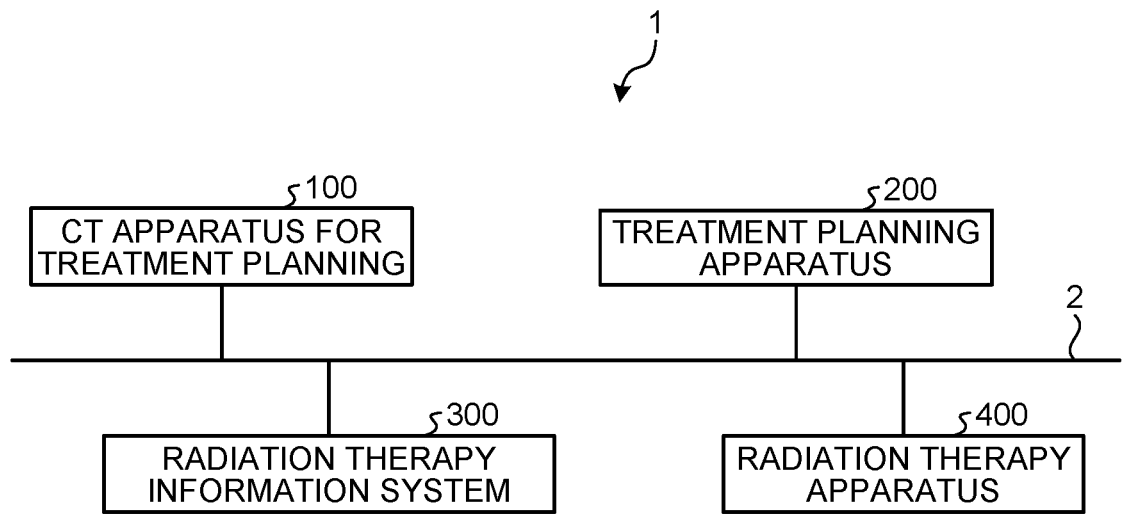
FIG. 1 is a diagram illustrating an example of a configuration of a radiation therapy system according to a first embodiment.

First, a radiation therapy system including a radiation therapy apparatus according to the present embodiment will be described. FIG. 1 is a diagram illustrating an example of a configuration of a radiation therapy system 1 according to a first embodiment. As illustrated in FIG. 1, the radiation therapy system 1 according to the first embodiment includes a computed tomography (CT) apparatus 100 for treatment planning, a treatment planning apparatus 200, a radiation therapy information system 300, and a radiation therapy apparatus 400. The CT apparatus 100 for treatment planning, the treatment planning apparatus 200, the radiation therapy information system 300, and the radiation therapy apparatus 400 are communicably connected to one another via a network 2. Note that the configuration illustrated in FIG. 1 is merely an example and the embodiments are not limited thereto. For example, various apparatuses and systems may also be included in the radiation therapy system 1.

The CT apparatus 100 for treatment planning has a gantry, a table with a tabletop, and a console, and collects CT image data including a treatment target site (tumor and the like) of a treatment subject lying on the tabletop and transmits the collected CT image data to the treatment planning apparatus 200. Specifically, the CT apparatus 100 for treatment planning collects projection data while rotating an X-ray tube and an X-ray detector provided on the gantry around the treatment subject, and reconstructs three-dimensional CT image data on the basis of the collected projection data. The tabletop in the CT apparatus 100 for treatment planning has a planar shape similarly to a tabletop of the radiation therapy apparatus.

In the present embodiment, only the CT apparatus 100 for treatment planning is illustrated as an apparatus for collecting image data for treatment planning; however, the embodiments are not limited thereto. For example, three-dimensional image data for treatment planning may also be collected by a magnetic resonance imaging (MRI) apparatus for treatment planning, an ultrasonic diagnostic apparatus, and the like.

The treatment planning apparatus 200 makes a treatment plan of radiation therapy by the radiation therapy apparatus 400 by using the three-dimensional CT image data of the treatment subject collected by the CT apparatus 100 for treatment planning. For example, the treatment planning apparatus 200 specifies the position of the treatment target site in the treatment subject by using the CT image data collected by the CT apparatus 100 for treatment planning. Furthermore, for example, the treatment planning apparatus 200 specifies the position of an organ at risk in the treatment subject by using the CT image data collected by the CT apparatus 100 for treatment planning. The treatment planning apparatus 200 makes a plan such as the irradiation angle of radiation to be applied by the radiation therapy apparatus 400, a dose and a shape of an irradiation field for each irradiation angle, and the number of irradiations so as to satisfy the following two conditions, (1) the dose to treatment target site is equal to or greater than a predetermined target dose, (2) the dose to the organ at risk is equal to or less than a predetermined permissive dose. Then, the treatment planning apparatus 200 transmits the treatment plan to the radiation therapy information system 300 and the radiation therapy apparatus 400.

The radiation therapy information system 300 stores and manages various information on radiation therapy. Specifically, the radiation therapy information system 300 stores and manages, for each treatment subject, various information on the progress of treatment, such as a treatment plan, CT image data, the position and shape of a treatment target site, the position and shape of an organ at risk, history information (irradiation history), various reports, and recording of situations of treatment subjects. The radiation therapy information system 300 can be accessed by each apparatus connected to the network 2 and can provide the managed information.

The radiation therapy apparatus 400 performs radiation therapy by irradiating the treatment subject with radiation according to the treatment plan by the treatment planning apparatus 200. Specifically, the radiation therapy apparatus 400 performs radiation therapy by a method in which X-rays or particle beams are irradiated while rotating the gantry (VMAT or particle arc therapy).

Figure 2:
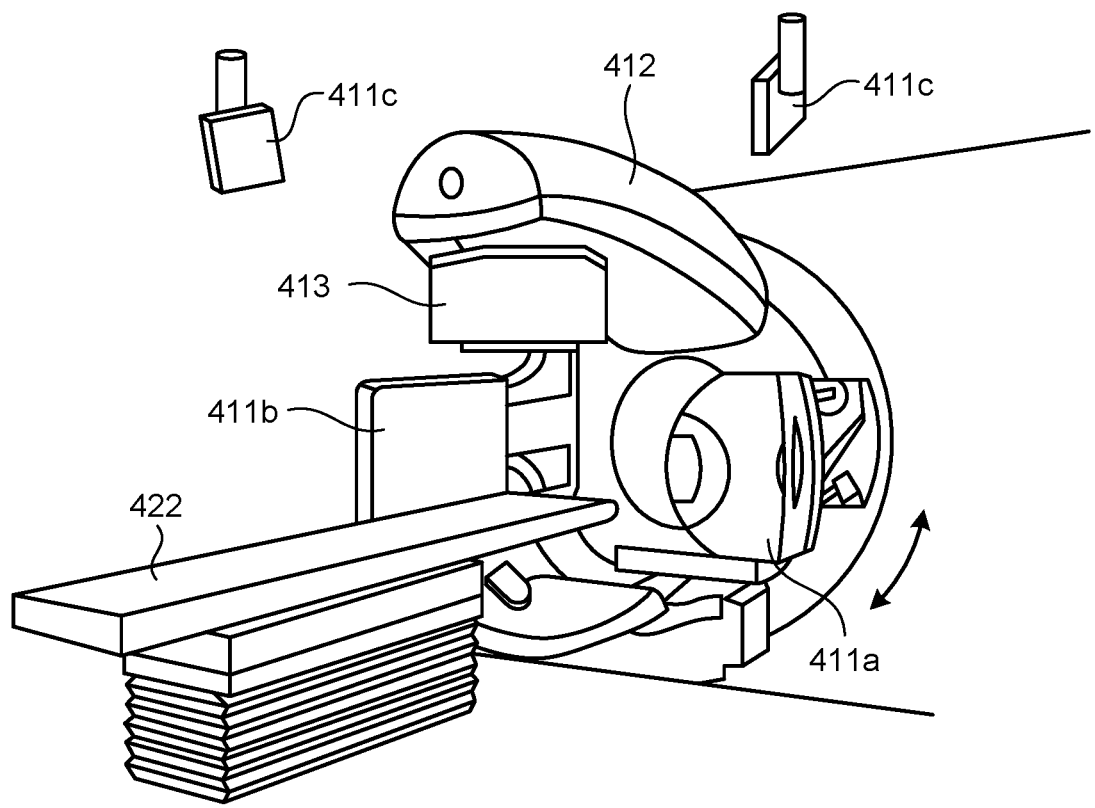
FIG. 2 is an external view illustrating an example of a radiation therapy apparatus according to the first embodiment.

FIG. 2 is an external view illustrating an example of the radiation therapy apparatus 400 according to the first embodiment. FIG. 2 illustrates the radiation therapy apparatus 400 installed in a treatment room. As illustrated in FIG. 2, the radiation therapy apparatus 400 includes a gantry having a radiation generator 412, a collimator 413, and an imaging device (an X-ray generator 411a and an X-ray detector 411b), and a table with a tabletop 422, and performs radiation therapy under the control of a console (not illustrated). Specifically, the radiation therapy apparatus 400 acquires the treatment plan from the radiation therapy information system 300. Then, the radiation therapy apparatus 400 performs radiation therapy on a treatment subject lying on the tabletop 422 in accordance with the treatment plan by rotating the gantry in the direction of an arrow.

In the radiation therapy, first, three-dimensional CT image data required for making a treatment plan is collected by the CT apparatus 100 for treatment planning. Here, a immobilization device may be provided to improve the reproducibility and retention of the posture of a treatment subject. Furthermore, marks required for setting the radiation irradiation area roughly at isocenter at each time of radiation therapy are attached to the body surface of the treatment subject. The isocenter is defined as intersection points of gantry rotation axis and center axis of beams.

Furthermore, in the treatment plan, an irradiation area of the radiation, an irradiation angle of the radiation, a dose and a shape of an irradiation field for each irradiation angle, the number of irradiations, and the like are determined. For example, in determining the irradiation area of the radiation, first, an organ at risk, which needs to be avoided from the radiation, is set on the basis of the CT image data collected by the CT apparatus 100 for treatment planning, and the like. Then, a gross tumor volume (GTV), which is a three-dimensional area where the growth and existence of a tumor is visible to the naked eye, is set, and a clinical target volume (CTV), which includes the set GTV and a potential tumor area not visible to the naked eye, is set. Note that the organ at risk, the GTV, and the CTV are set by, for example, contouring (extraction of contours); however, the contouring can also be performed by either manual processing by a doctor or automatic processing by an image processing technology.

Furthermore, in determining the irradiation area of the radiation, an internal target volume (ITV) including an internal margin (IM) for absorbing the influence of the movement of internal organs such as respiration, swallowing, heartbeat, and peristalsis is set for the CTV. Moreover, the irradiation area of the radiation is determined by setting a planning target volume (PTV) including a setting error (SM: set-up margin) in each irradiation with respect to the CTV.

When the irradiation area of the radiation is determined in this way, irradiation conditions of the radiation for the determined irradiation area are set. For example, in the treatment planning apparatus 200, an operator (medical worker) sets irradiation conditions such as a dose and a shape of an irradiation field for each irradiation angle of radiation, and the number of irradiations. The shape of the irradiation field is formed by, for example, a multi-leaf collimator (MLC) which is the collimator 413. The MLC has a plurality of radiation shielding plates for setting the irradiation range of radiation, and each radiation shielding plate is independently driven on the basis of the treatment plan, so that an irradiation field matching the shape of the irradiation area (PTV) of the radiation can be formed.

The treatment plan generated in this way is transmitted to the radiation therapy information system 300 and managed together with patient information, treatment history, and the like. At the time of radiation therapy, the treatment plan is transmitted from the radiation therapy information system 300 to the radiation therapy apparatus 400. The radiation therapy apparatus 400 irradiates the treatment subject lying on the tabletop 422 with radiation in accordance with the received treatment plan.

In order that the radiation irradiation area in the treatment subject lying on the tabletop 422 is located in an isocenter of the radiation therapy apparatus 400, the posture of the treatment subject, the table, and the like are adjusted so that the marks attached to the body surface of the treatment subject overlap laser from a laser aligner, so rough alignment is performed.

Thereafter, the radiation therapy apparatus 400 generates cone beam CT image data for alignment by the imaging device including the X-ray generator 411a and the X-ray detector 411b in order to perform alignment between the irradiation area of the radiation and the isocenter of the radiation therapy apparatus 400. For example, the radiation therapy apparatus 400 emits X-rays from the X-ray generator 411a while rotating the gantry, collects projection data for angles of 200° or more, and reconstructs three-dimensional cone beam CT image data on the basis of the collected projection data.

The radiation therapy apparatus 400 performs alignment between the irradiation area and the isocenter by using the reconstructed cone beam CT image data and the CT image data for treatment planning. Note that the radiation therapy apparatus 400 can also perform alignment by other methods in addition to the alignment using the aforementioned cone beam CT image data. For example, as illustrated in FIG. 2, two X-ray imaging devices 411c are installed in the treatment room as imaging devices. The radiation therapy apparatus 400 captures the treatment subject lying on the tabletop 422 by the two X-ray imaging devices 411c, and compares the obtained X-ray images in two directions with a digitally reconstructed radiograph (DRR) generated from the CT image data for treatment planning, thereby performing alignment between the irradiation area and the isocenter. Note that the DRR is a virtual X-ray imaged image obtained by projecting the CT image data for treatment planning in two directions taken by the two X-ray imaging devices 411c.

Then, the radiation therapy apparatus 400 performs irradiation with radiation in accordance with the treatment plan. Here, the radiation therapy apparatus 400 according to the present embodiment performs radiation therapy by the VMAT or the particle arc therapy. Specifically, the radiation therapy apparatus 400 performs radiation therapy on an organ with a respiratory motion by the gate irradiation in which irradiation is performed only when respiration of a treatment subject is in a desired phase.

Figure 3:
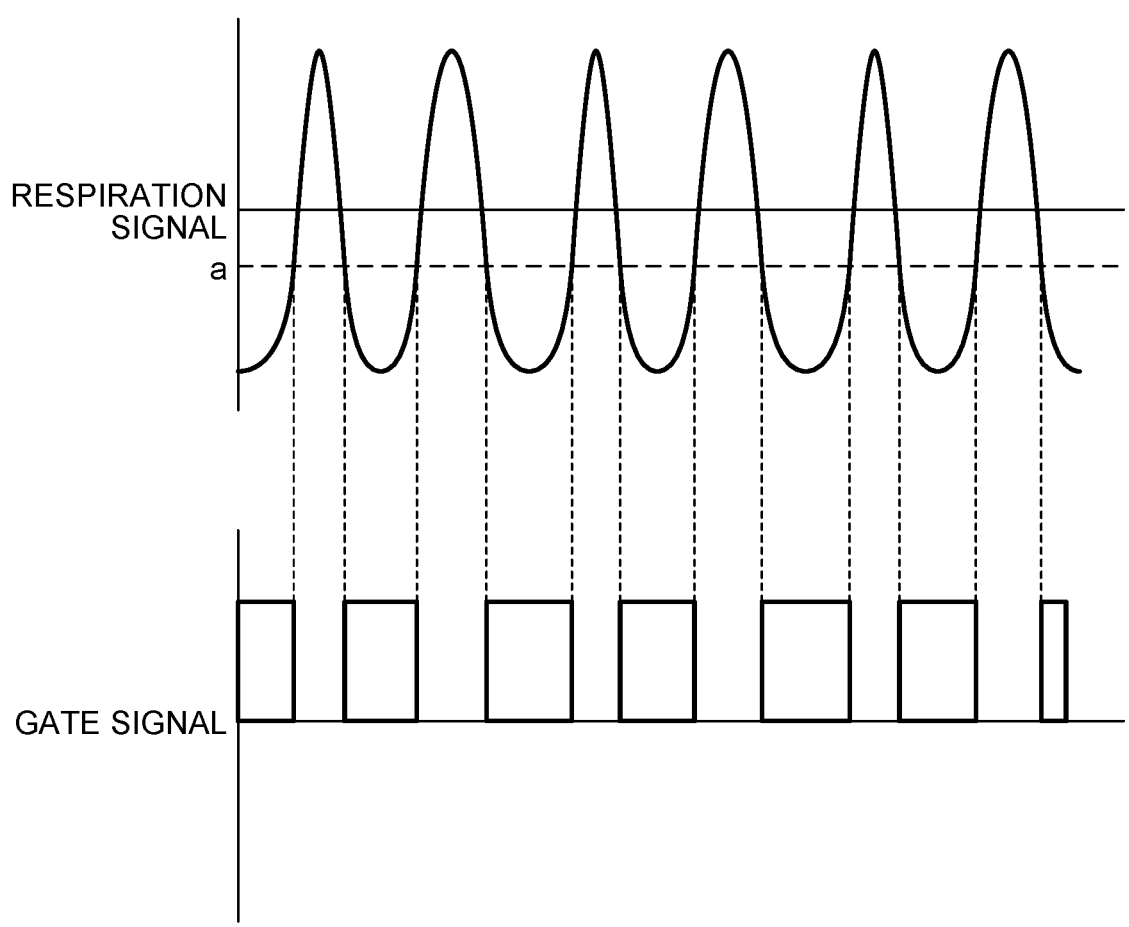
FIG. 3 is a diagram for explaining gate irradiation according to the first embodiment.

FIG. 3 is a diagram for explaining gate irradiation according to the first embodiment. In FIG. 3, the upper part indicates a respiration signal and the lower part indicates a gate signal. For example, in the gate irradiation, a gate signal for applying radiation is transmitted on the basis of a respiration signal acquired from the treatment subject, and radiation is applied only when the gate signal is ON.

As an example, the respiration signal indicates an amplitude corresponding to respiration as illustrated in the upper part of FIG. 3. In the gate irradiation, a threshold a (for example, 30% of the amplitude) is set for the amplitude of the respiration signal, the gate signal is ON only when the respiration signal is less than the set threshold, and radiation is applied while the gate signal is ON.

Since the respiration has almost no reproducibility, the lengths of gate signals based on the respiration signals are different one by one. Furthermore, when a baseline shift occurs in which the respiration signal shifts upward or downward with time, the length of the gate signal changes significantly. Therefore, when the gate irradiation is performed as is, a dose may significantly deviate from a target administration dose. For example, when a radiation dose rate is kept as the treatment plan and rotation radiation is performed on the basis of the respiration signal shifted upward, the gate signal is shorter than in the lower part of FIG. 3, and as a consequence, the dose is lower than the target administration dose. On the other hand, when the radiation dose rate is kept as the treatment plan and rotation radiation is performed on the basis of the respiration signal shifted downward, the gate signal is longer than in the lower part of FIG. 3, and as a consequence, the dose is higher than the target administration dose.

In this regard, the radiation therapy apparatus 400 according to the present embodiment monitors the respiration of the treatment subject and changes at least one of the dose rate of radiation to be applied to the treatment subject and the rotation speed of the gantry, on the basis of the result of the monitoring, thereby allowing an administration dose to be stably secured while preventing the following two cases, (1) an increase in radiation exposure to a normal tissue, (2) a decrease in radiation exposure to the irradiation area.

Figure 4:
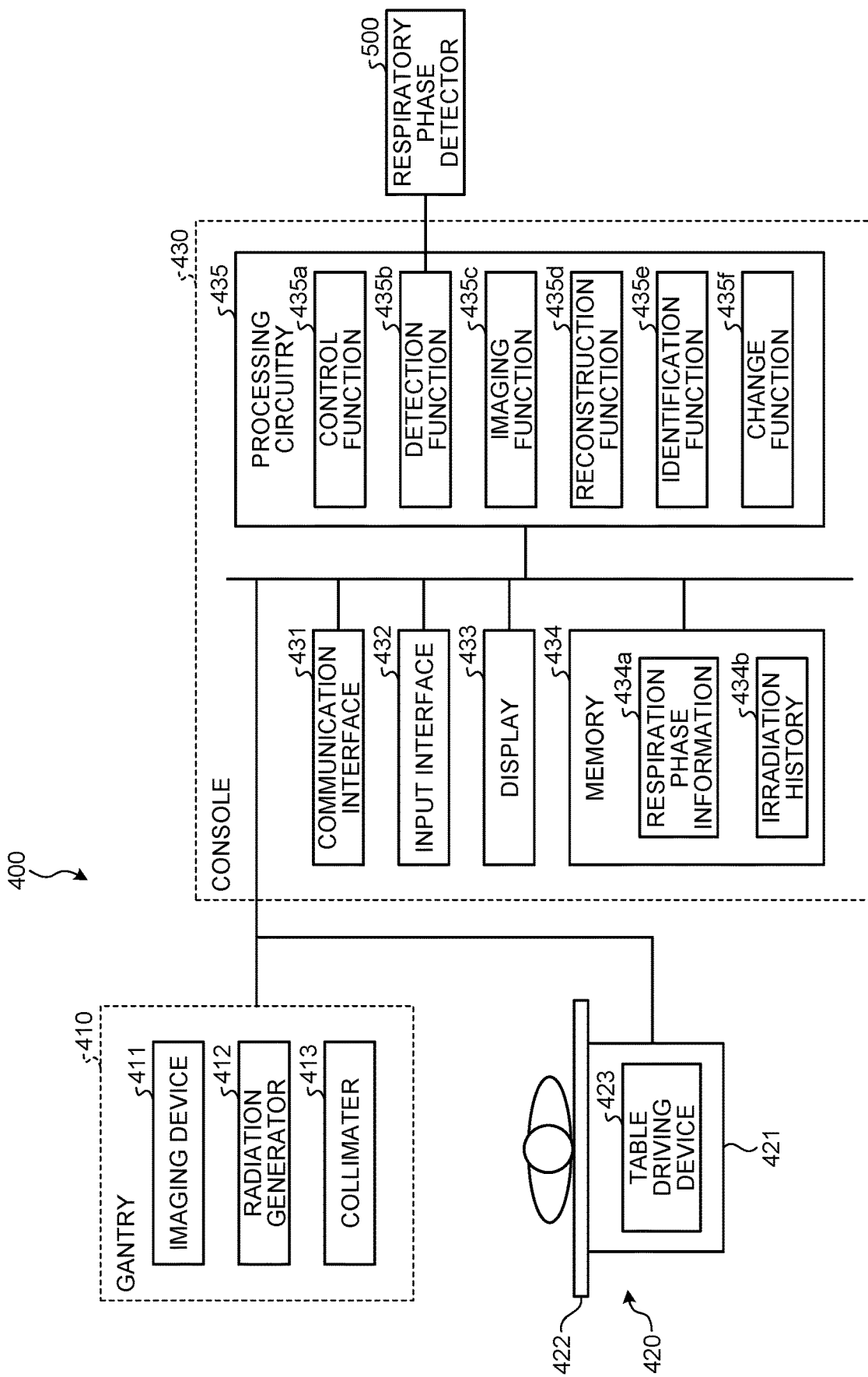
FIG. 4 is a diagram illustrating an example of a configuration of the radiation therapy apparatus according to the first embodiment.

Hereinafter, details of the radiation therapy apparatus 400 according to the present embodiment will be described. FIG. 4 is a diagram illustrating an example of the configuration of the radiation therapy apparatus 400 according to the first embodiment. As illustrated in FIG. 4, the radiation therapy apparatus 400 includes a gantry 410, a table 420, and a console 430, and a respiratory phase detector 500 is connected to the radiation therapy apparatus 400.

The respiratory phase detector 500 acquires respiration information of the treatment subject and transmits a respiration signal indicating the acquired respiration information to the console 430. For example, the respiratory phase detector 500 is a detector that fastens a belt around the abdomen of the treatment subject and detects respiration on the basis of tension applied to the belt, a detector that brings a rod-shaped contact part into contact with the abdomen and detects respiration on the basis of pressure applied to the contact part, a detector that attaches a sensor for measuring the flow rate of air to a nose or a mouth and detects respiration on the basis of the flow rate of air from the nose or the mouth, a detector that measures the shape of a body surface in real time and detects respiration on the basis of the position of the abdomen or chest, and the like. Furthermore, as a method of detecting a respiratory phase, a method of imaging an X-ray image in real time by an imaging device 411 and detecting respiration from the position and the like of a diaphragm in the imaged image may be used. In such a case, a means for detecting the respiratory phase is included in the radiation therapy apparatus 400.

The gantry 410 includes the imaging device 411, the radiation generator 412, and the collimator 413. The imaging device 411 includes the X-ray generator 411a and the X-ray detector 411b, and performs capturing for collecting the cone beam CT image data of the treatment subject placed on the table 420 under the control of the console 430. Specifically, in the imaging device 411, the X-ray generator 411a that emits X-rays for capturing and the X-ray detector 411b that detects the X-rays for capturing are arranged to face each other with the treatment subject interposed therebetween. Furthermore, the imaging device 411 emits X-rays from the X-ray generator 411a during the rotation of the gantry 410 and detects the X-rays by the X-ray detector 411b, thereby collecting projection data for angles of 200° or more. The imaging device 411 transmits the collected projection data to the console 430.

The radiation generator 412 includes an electron gun and an acceleration tube (not illustrated). The acceleration tube accelerates thermions generated from the electron gun, and allows the thermions to collide with a tungsten target to emit therapeutic radiation.

The collimator 413 is, for example, an MLC, and has a plurality of radiation shielding plates for setting the irradiation range of the therapeutic radiation. For example, the collimator 413 independently moves the radiation shielding plates by a movement mechanism (not illustrated) under the control of the console 430, thereby forming the irradiation field of radiation having a shape corresponding to the irradiation area of the treatment subject.

The table 420 has a base unit 421 and a tabletop 422. The base unit 421 has a table driving device 423 therein and movably supports the tabletop 422. The tabletop 422 has a planar shape and a treatment subject is placed thereon. The table driving device 423 includes a motor, an actuator, and the like and moves the tabletop 422 under the control of the console 430.

The console 430 has a communication interface 431, an input interface 432, a display 433, a memory 434, and processing circuitry 435.

The communication interface 431 is connected to the processing circuitry 435, and controls transmission and communication of various data performed with each device connected via the network 2. For example, the communication interface 431 is implemented by a network card, a network adaptor, a network interface controller (NIC), and the like.

The input interface 432 is connected to the processing circuitry 435, converts an input operation received from the operator (medical worker) into an electric signal, and outputs the electric signal to the processing circuitry 435. Specifically, the input interface 432 converts the input operation received from the operator into the electric signal and outputs the electric signal to the processing circuitry 435. For example, the input interface 432 is implemented by a trackball, a switch button, a mouse, a keyboard, a touch panel for performing an input operation by touching an operation surface, a touch screen in which a display screen and a touch pad are integrated, a non-contact input circuit using an optical sensor, a voice input circuit, and the like. Note that in the present specification, the input interface 432 is not limited to one including physical operation parts such as a mouse and a keyboard. For example, an example of the input interface 432 also includes an electric signal processing circuit that receives an electric signal corresponding to an input operation from an external input device provided separately from the device and outputs the electric signal to a control circuit.

The display 433 is connected to the processing circuitry 435, and displays various information and various image data output from the processing circuitry 435. For example, the display 433 is implemented by a liquid crystal display, a cathode ray tube (CRT) display, an organic EL display, a plasma display, a touch panel, and the like. In the present embodiment, for example, the display 433 displays the treatment plan, the irradiation history, and the like.

The memory 434 is connected to the processing circuitry 435 and stores various data. For example, the memory 434 is implemented by a semiconductor memory element such as a random access memory (RAM) and a flash memory, a hard disk, an optical disk, or the like. As an example, the memory 434 stores respiration phase information 434a, irradiation history 434b, and the like. Furthermore, the memory 434 stores the treatment plan received from the radiation therapy information system 300, various processing results, and the like. Furthermore, the memory 434 stores computer programs corresponding to various functions that are performed by the processing circuitry 435.

The respiration phase information 434a is the respiration information of the treatment subject detected by the respiratory phase detector 500. For example, the respiration phase information 434a is a respiration signal acquired from the treatment subject placed on the tabletop 422.

The irradiation history 434b includes the irradiation conditions of radiation actually applied to the treatment subject, a dose distribution, and the like, and is stored in the memory 434 each time radiation irradiation is performed. The irradiation history 434b is transmitted to the radiation therapy information system 300 each time the radiation irradiation is completed, and is managed by the radiation therapy information system 300.

The processing circuitry 435 controls the overall operation of the radiation therapy apparatus 400 in response to the input operation received from the operator via the input interface 432. For example, the processing circuitry 435 is implemented by a processor. As illustrated in FIG. 3, the processing circuitry 435 performs a control function 435a, a detection function 435b, an imaging function 435c, a reconstruction function 435d, an identification function 435e, and a change function 435f. The processing circuitry 435 is an example of processing circuitry.

The control function 435a performs control to perform processing according to various requests input via the input interface 432. For example, the control function 435a controls transmission/reception of information (for example, the treatment plan, the irradiation history, and the like) via the communication interface 431, storage of information to the memory 434, display of information on the display 433, and the like.

Furthermore, the control function 435a transmits a control signal based on the treatment plan, thereby controlling the rotation of the gantry 410, the irradiation of radiation by the radiation generator 412, the movement of the radiation shielding plate in the collimator 413, and the like. Furthermore, the control function 435a transmits the control signal based on the treatment plan to control the table driving device 423 in the table 420, thereby controlling the movement of the tabletop 422.

The control function 435a controls radiation therapy in which radiation is applied while rotating the gantry 410. Specifically, the control function 435a allows radiation to be applied while rotating the gantry 410, and controls the irradiation and stop of the radiation during the rotation of the gantry 410 on the basis of the respiration of the treatment subject. More specifically, the control function 435a rotates the gantry 410 by transmitting the control signal to the gantry 410. Moreover, the control function 435a transmits a gate signal to the gantry 410 by comparing the respiration signal of the treatment subject detected by the detection function 435b with a threshold, thereby controlling radiation therapy by the gate irradiation based on the respiration signal of the treatment subject. Furthermore, the control function 435a controls radiation irradiation at a dose rate changed by the change function 435f, and the rotation of the gantry 410 at a rotation speed changed by the change function 435f. The above control will be described below.

The detection function 435b detects the respiration of the treatment subject. Specifically, the detection function 435b detects the respiration signal of the treatment subject by performing a medical examination on the basis of the signal from the respiratory phase detector 500.

The imaging function 435c controls the imaging device 411 to collect projection data for reconstructing the cone beam CT image data. Specifically, the imaging function 435c controls the rotation of the gantry 410, the irradiation of X-rays by the X-ray generator 411a, the data collection by the X-ray detector 411b. For example, the imaging function 435c allows the X-ray generator 411a to emit X-rays while rotating the gantry 410 by 200° or more, and collects data with the X-ray detector 411b, thereby collecting projection data for angles of 200° or more around the treatment subject. When performing radiation therapy by the gate irradiation, the imaging function 435c may collect projection data only in exhalation on the basis of the respiration signal received from the respiratory phase detector 500, or may continuously collect projection data regardless of the respiration signal. Then, the imaging function 435c stores the collected projection data in the memory 434.

Furthermore, when the two X-ray imaging devices 411c are installed in the treatment room, the imaging function 435c controls the two X-ray imaging devices 411c, thereby collecting X-ray images in two directions and storing the collected X-ray image in two directions in the memory 434. When performing radiation therapy by the gate irradiation, the imaging function 435c collects X-ray images of exhaled breath on the basis of the respiration signal received from the respiratory phase detector 500.

The reconstruction function 435d generates various images from the projection data collected by the imaging function 435c, and stores the generated image in the memory 434. For example, the reconstruction function 435d reconstructs the cone beam CT image data by reconstructing the projection data collected only in exhalation, by various reconstruction methods, and stores the reconstructed cone beam CT image data in the memory 434. Alternatively, the reconstruction function 435d continuously divides the projection data into projection data for each respiratory phase regardless of the respiration signal, reconstructs the cone beam CT image data (4D data) by reconstructing the divided projection data for each phase by various reconstruction methods, and stores the reconstructed cone beam CT image data in the memory 434.

The identification function 435e identifies the positional relationship between the isocenter and the irradiation area of radiation in the radiation therapy apparatus 400 on the basis of image data. For example, the identification function 435e identifies conversion (rotation or movement) parameters of the cone beam CT image data so as to substantially match tumor, organ, bone structure, and the like on the CT image at the time of planning. Moreover, the identification function 435e calculates 6-axis parameters of the position and angle of the tabletop 422 to substantially match anatomical structures of the CT image at the time of planning and the cone beam CT on the basis of the specified positional relationship.

Furthermore, for example, the identification function 435e compares the X-ray images in two directions captured by the two X-ray imaging devices 411c with DRR generated assuming that the CT image data for treatment planning is at a position planned for treatment, thereby identifying conversion (rotation or movement) parameters between the coordinate system of the radiation therapy apparatus 400 and the CT image data for treatment planning at the planned position. Then, the identification function 435e calculates 6-axis parameters of the position and angle of the tabletop 422 so that an anatomical structure of the treatment subject at the time of X-ray image collection substantially matches the CT image at the time of planning, on the basis of the specified conversion parameters.

The change function 435f predicts an administration dose on the basis of a respiratory phase range (a period of time when the respiration signal is below the threshold) in which the radiation is applied in the respiration of the treatment subject, and changes at least one or both of the dose rate of the radiation to be applied to the treatment subject and the rotation speed of the gantry so that the administration dose reaches a target dose. Specifically, the change function 435f estimates a period during which the gate signal is ON, on the basis of the respiration signal of the treatment subject lying on the tabletop 422, and predicts the administration dose when the radiation is applied in the estimated period. Then, the change function 435f compares the predicted administration dose with the target dose planned in the treatment plan, and changes at least one or both of the dose rate of the radiation and the rotation speed of the gantry so that the administration dose reaches the target dose.

Furthermore, the change function 435f changes at least one or both of the dose rate of the radiation and the rotation speed of the gantry on the basis of the comparison result between the administration dose of the radiation applied in the respiratory phase range and the planned dose during the rotation of the gantry 410. That is, the change function 435f monitors a deviation between the planned dose and the administration dose by comparing the dose actually administrated during the rotation irradiation with the planned dose, and finely adjusts a subsequent plan when the deviation exceeds a certain range.

Figure 5:
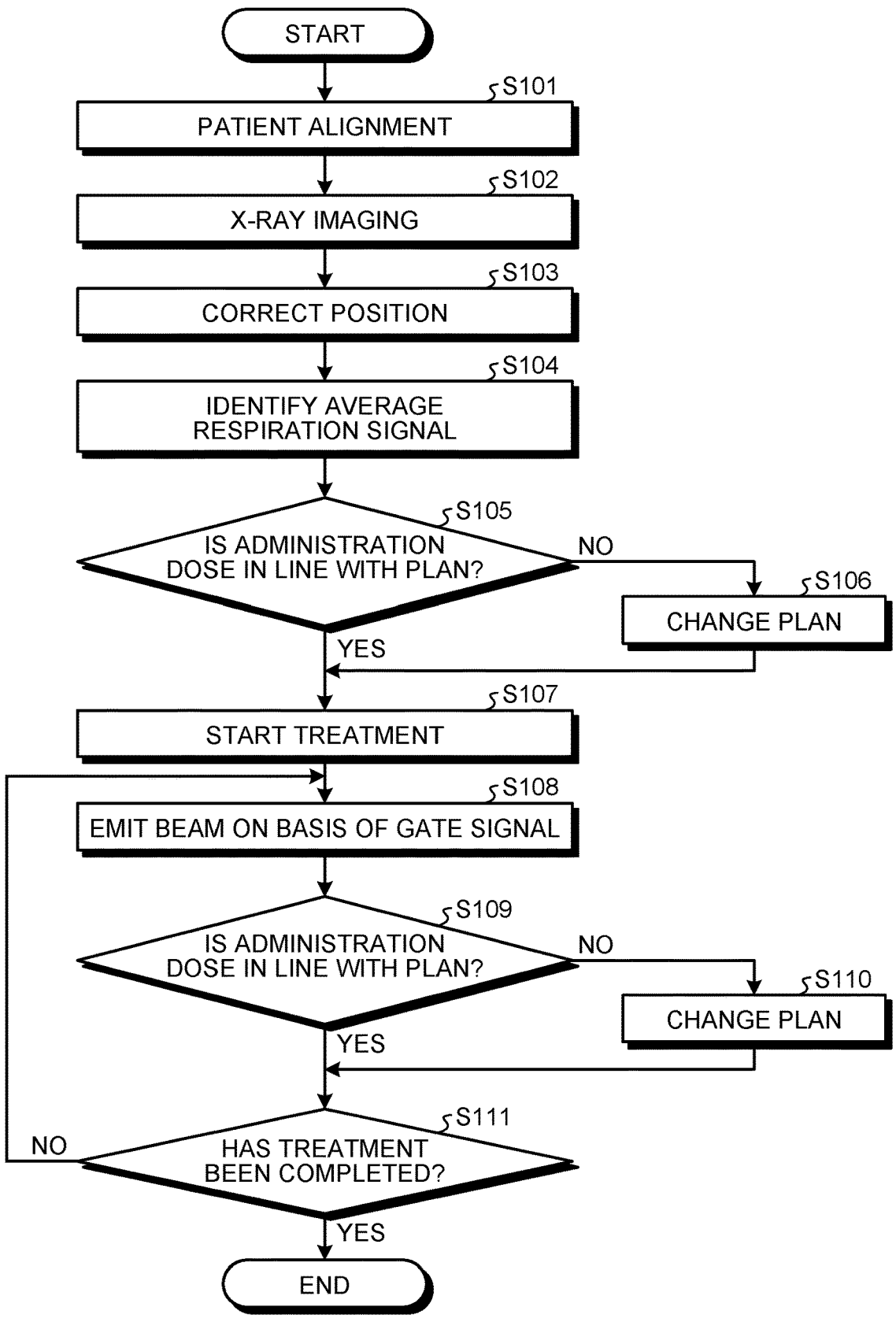
FIG. 5 is a flowchart illustrating a processing procedure by the radiation therapy apparatus according to the first embodiment.

Hereinafter, an example of processing performed by the radiation therapy apparatus 400 will be described with reference to FIG. 5. FIG. 5 is a flowchart illustrating a processing procedure performed by the radiation therapy apparatus 400 according to the first embodiment. In FIG. 5, steps S101, S107, S108, and S111 are performed, for example, by the processing circuitry 435 that reads a computer program corresponding to the control function 435a from the memory 434 and executes the read computer program. Furthermore, step S102 is performed, for example, by the processing circuitry 435 that reads computer programs corresponding to the control function 435a and the imaging function 435c from the memory 434 and executes the read computer programs. Furthermore, step S103 is performed, for example, by the processing circuitry 435 that reads computer programs corresponding to the control function 435a and the identification function 435e from the memory 434 and executes the read computer programs. Furthermore, step S104 is performed, for example, by the processing circuitry 435 that reads a computer program corresponding to the detection function 435b from the memory 434 and executes the read computer program. Furthermore, steps S105, S106, S109, and S110 are performed, for example, by the processing circuitry 435 that reads a computer program corresponding to the change function 435f from the memory 434 and executes the read computer program.

In the radiation therapy apparatus 400 according to the first embodiment, first, a medical staff places a treatment subject on the tabletop 422 and adjusts the table 420 so that a mark on the body surface matches a laser mark from the laser aligner. The control function 435a controls the table 420 in response to an operation of the medical staff, thereby performing patient alignment as illustrated in FIG. 5 (step S101).

When the patient alignment is completed, the control function 435a and the imaging function 435c perform X-ray imaging in response to an operation of the medical staff (step S102). For example, the control function 435a rotates the gantry 410 at a start angle of the rotation irradiation. Then, when the rotation of the gantry 410 is completed and the gantry 410 is set in the irradiation start direction, the imaging function 435c performs X-ray imaging.

For example, the imaging function 435c collects X-ray images in two directions by controlling the two X-ray imaging devices 411c. Furthermore, for example, the imaging function 435c repeatedly captures X-ray images while rotating the gantry 410 from the rotation start angle. When the X-ray images are continuously captured by the imaging function 435c, the reconstruction function 435d three-dimensionally reconstructs the captured X-ray images on the basis of respiratory phase data collected in correlation with the capturing of the X-ray images. That is, the reconstruction function 435d reconstructs three-dimensional image data corresponding to a respiratory phase to be irradiated with radiation. Note that the reconstruction function 435d can also perform four-dimensional reconstruction that reconstructs a plurality of three-dimensional image data corresponding to a plurality of respiratory phases, on the basis of the continuously collected X-ray images.

When the X-ray imaging is performed in this way, the identification function 435e corrects the position on the basis of the image data as illustrated in FIG. 5 (step S103). For example, the identification function 435e compares the CT image data collected by the CT apparatus 100 for treatment planning with the cone beam CT image data, and identifies the positional relationship between the CT image data at the time of planning and the cone beam CT image data. Then, the identification function 435e calculates the 6-axis parameters of the position and angle of the tabletop 422 on the basis of the specified positional relationship.

Alternatively, the identification function 435e compares the X-ray images in two directions captured by the two X-ray imaging devices 411c with the DRR generated assuming that the CT image data for treatment planning is at the position planned for treatment, thereby identifying the positional relationship so that the anatomical structure of the treatment subject at the time of X-ray image collection in the radiation therapy apparatus 400 substantially matches the CT image at the time of planning and calculating the 6-axis parameters of the position and angle of the tabletop 422. Note that the identification function 435e can further confirm the position by capturing the X-ray images in two directions after alignment using the cone beam CT image data is performed.

When the position is corrected as described above, the detection function 435b identifies an average respiration signal on the basis of the respiration signal acquired from the treatment subject on the tabletop 422 (step S104). For example, the detection function 435b continuously (when no radiation exposure exists) or intermittently (when radiation exposure exists) detects the respiratory phase of the treatment subject during the period until the treatment beam is emitted after the treatment subject is placed on the tabletop 422. Then, the detection function 435b evaluates the respiratory stability of the treatment subject and simultaneously averages respiration signals for a certain period of time to identify an average respiration signal of the treatment subject at the time before treatment.

Thereafter, the change function 435f determines whether the administration dose is in line with the plan (step S105). Specifically, the change function 435f calculates the length of the gate signal by calculating the period during which the average respiration signal identified by the detection function 435b is less than the threshold. Then, the change function 435f calculates an administration dose when radiation is applied at the dose rate in the treatment plan and the calculated length of the gate signal, calculates an error with the target dose, and determines whether the error exceeds the threshold.

As an example, it is assumed that irradiation is performed 12 times on the basis of the respiration signal of the treatment subject during one rotation of the gantry 410 and the target dose is "2 Gy". In such a case, the change function 435f calculates an administration dose when radiation is applied at the dose rate in the treatment plan and the length of the gate signal based on the average respiration signal at each of 12 irradiation angles, compares the calculated administration dose with the target dose "2 Gy", and determines whether an error is within a certain range (for example, within 3% of 2 Gy).

When the administration dose is in line with the plan (Yes at step S105), the control function 435a starts treatment (step S107) and emits beams on the basis of the gate signal (step S108). For example, when the error between the calculated administration dose and the target dose "2 Gy" is within "3% of 2 Gy", the control function 435a performs irradiation with radiation according to the treatment plan in a radiation irradiation period based on the gate signal.

However, when the administration dose is not in line with the plan (No at step S105), the change function 435f changes the treatment plan (step S106). Then, the control function 435a starts treatment in accordance with the changed plan (step S107). For example, when the error between the calculated administration dose and the target dose "2 Gy" exceeds "3% of 2 Gy", the change function 435f changes at least one or both of the dose rate of the radiation and the rotation speed of the gantry 410 so that the error between the administration dose and the target dose "2 Gy" is within "3% of 2 Gy". Then, the control function 435a performs control according to the change with respect to at least one or both of the dose rate of the radiation and the rotation speed of the gantry.

As described above, when it is determined that the treatment plan is changed or not changed, the control function 435a allows beams to be emitted in response to the gate signal while rotating the gantry 410 from a treatment start angle (step S108).

Then, when the beams are emitted on the basis of the gate signal, the change function 435f determines whether the administration dose is in line with the plan during the rotation irradiation (step S109). Specifically, the change function 435f calculates an error between the administration dose of the actually applied radiation and the treatment plan, and determines whether the error exceeds the threshold. For example, the change function 435f determines whether the administration dose of the actually applied radiation is less than 3% from the treatment plan when the rotation of the gantry 410 has been completed by ⅓.

When the administration dose is in line with the plan (Yes at step S109), the control function 435a determines whether the treatment has been completed (step S111). For example, when the administration dose of the actually applied radiation is not less than 3% from the treatment plan, the control function 435a determines whether the treatment has been completed.

However, when the administration dose is not in line with the plan (No at step S109), the change function 435f changes the treatment plan (step S110) and determines whether the treatment has been completed (step S111). For example, when the administration dose of the actually applied radiation is less than 3% from the treatment plan, the change function 435f changes at least one or both of the dose rate of the radiation and the rotation speed of the gantry 410. As an example, the change function 435f increases the dose rate in subsequent irradiation and cancels the error of 3% with remaining ⅔ rotation.

When the treatment has not been completed in step S111 (No at step S111), the control function 435a returns to step S108 and emits beams on the basis of the gate signal. However, when the treatment has been completed (Yes at step S111), the control function 435a ends the process.

As described above, according to the first embodiment, the detection function 435b detects respiration of a treatment subject. The change function 435f predicts an administration dose on the basis of a respiratory phase range in which radiation is applied in the respiration of the treatment subject, and changes at least one or both of the dose rate of the radiation to be applied to the treatment subject and the rotation speed of the gantry 410 so that the administration dose reaches a target dose. The control function 435a performs control according to the change with respect to at least one or both of the dose rate of the radiation and the rotation speed of the gantry 410. Consequently, the radiation therapy apparatus 400 according to the first embodiment can flexibly change a treatment plan in accordance with the respiratory state of the treatment subject, and to stably secure an administration dose while preventing an increase in radiation exposure to a normal tissue and a decrease in radiation exposure to the irradiation area.

Furthermore, according to the first embodiment, the detection function 435b identifies latest average respiration information on the basis of respiration information of the treatment subject. The change function 435f detects a respiratory phase range on the basis of the average respiration information. Consequently, the radiation therapy apparatus 400 according to the first embodiment can detect a gate irradiation period for each treatment subject on the basis of latest respiration information.

Furthermore, according to the first embodiment, the change function 435f changes at least one or both of the dose rate of the radiation and the rotation speed of the gantry 410 on the basis of a comparison result between an administration dose of the radiation applied in the respiratory phase range and a planned dose during the rotation of the gantry 410. Consequently, the radiation therapy apparatus 400 according to the first embodiment can cope with a change in the respiration of the treatment subject during radiation irradiation, and more stably secure an administration dose.

Second Embodiment

In the second embodiment, a case where the rotation speed of the gantry 410 is changed in accordance with the irradiation period and stop period of radiation will be described. Note that the radiation therapy apparatus 400 according to the second embodiment is different in control by the control function 435a as compared with the first embodiment. Hereinafter, this will be mainly described.

The control function 435a according to the second embodiment changes the rotation speed of the gantry 410 in accordance with the irradiation period of radiation and the stop period of the radiation during the rotation of the gantry 410. Specifically, the control function 435a controls the rotation of the gantry 410 so that the rotation speed during the irradiation period of the radiation is relatively high and the rotation speed during the stop period of the radiation is relatively low.

Figure 6:
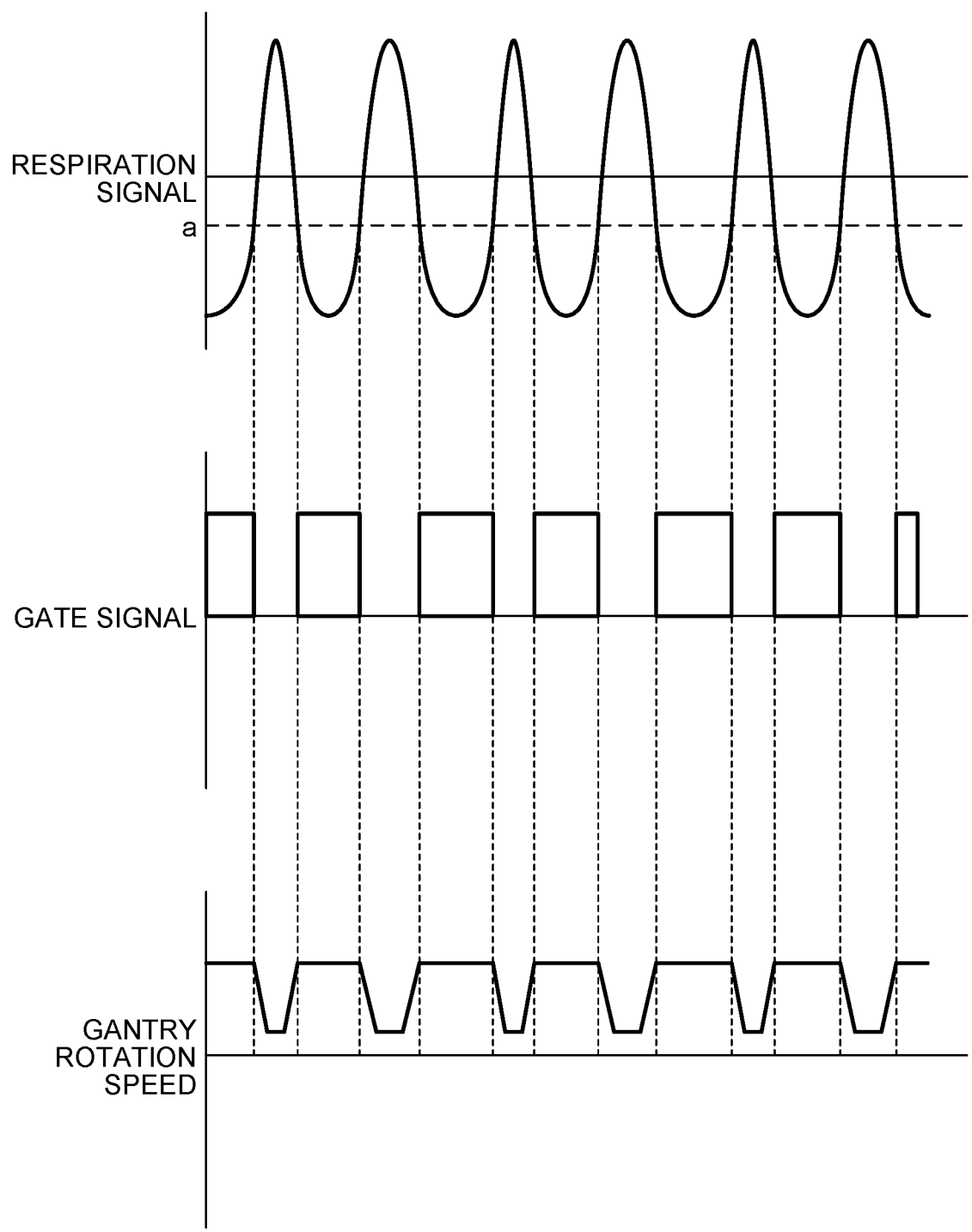
FIG. 6 is a diagram for explaining an example of control by a control function according to a second embodiment.

FIG. 6 is a diagram for explaining an example of control by the control function 435a according to the second embodiment. In FIG. 6, the upper part indicates a respiration signal, the intermediate part indicates a gate signal, and the lower part indicates the rotation speed of the gantry 410.

For example, the control function 435a compares the respiration signal illustrated in the upper part of FIG. 6 with a threshold "a" and transmits the gate signal to the gantry 410 in accordance with a respiratory phase below the threshold "a", thereby irradiating a respiratory phase corresponding to the gate signal with radiation. Moreover, the control function 435a controls the rotation of the gantry 410 so that the rotation speed of the gantry 410 is relatively high in the period during which the gate signal is transmitted and the radiation is applied and the rotation speed of the gantry 410 is relatively low in the period during which the gate signal is not transmitted and the radiation is stopped, as illustrated in the lower part of FIG. 6. With this, the radiation therapy apparatus 400 according to the second embodiment can stably secure a target dose without increasing a dose to a normal tissue in front of an irradiation direction with respect to a target to be irradiated with radiation.

FIG. 7 is a diagram illustrating irradiation angles of radiation applied by the radiation therapy apparatus 400 according to the second embodiment. In FIG. 7, the upper part indicates angles at which radiation is applied during one rotation of the gantry 410 in a state in which the rotation speed is constant, and the lower part indicates angles at which radiation is applied during one rotation of the gantry 410 while the rotation speed is changed. Specifically, in FIG. 7, an outer circle indicates a rotation trajectory and a region R1 indicates the irradiation angle of the radiation. That is, FIG. 7 illustrates a case where radiation is applied on the basis of the gate signal while a beam irradiation port facing the center direction of the circle rotates along the circle.

For example, when the rotation speed of the gantry 410 is set to a constant speed, the irradiation angles are sparse as illustrated in the upper part of FIG. 7. In order to administer a target dose in such a state, a dose rate needs to significantly increase as compared with the case of continuous irradiation during rotation. However, when the dose rate is increased, a dose to a normal tissue in front of the irradiation direction relatively increases.

Therefore, as illustrated in the gantry rotation speed of FIG. 6, the rotation speed during the radiation irradiation period (when the gate signal is ON) is made constant and the rotation speed during the radiation stop period (when the gate signal is OFF) is slowed down. With this, the rotation angle when the gate signal is OFF becomes small, and as illustrated in the lower part of FIG. 7, the irradiation angles of the radiation can be made dense. As a consequence, a target dose can be secured without significantly changing a dose rate as compared with the case of continuous irradiation during rotation.

The aforementioned embodiment can also be applied, for example, in combination with the formulation of a treatment plan by processing circuitry (not illustrated) in the treatment planning apparatus 200. For example, the processing circuitry in the treatment planning apparatus 200 performs the change function 435f described in the first embodiment and the predicted administration dose reaches the target dose; however, a dose to an organ at risk can be reduced without lowering the administration dose by applying the present embodiment when a limit to an organ at risk is exceeded.

In such a case, the processing circuitry in the treatment planning apparatus 200 acquires the average respiration signal of the treatment subject at the time before treatment and calculates the length of the gate signal. Then, the processing circuitry in the treatment planning apparatus 200 identifies a dose rate for reaching a target administration dose on the basis of the calculated length of the gate signal, and calculates an administration distribution when radiation is applied at the dose rate. When an administration dose to an organ at risk exceeds a limit in the administration distribution, the processing circuitry in the treatment planning apparatus 200 reduces the rotation speed during the stop period of the radiation irradiation without changing the rotation angle range in the formulated treatment plan, thereby allowing the radiation irradiation angles to be dense.

The processing circuitry in the treatment planning apparatus 200 allows the radiation irradiation angles to be dense by changing the rotation speed, and specifies conditions that an error between the administration dose and the target dose is within a certain range and an administration dose to an organ at risk does not exceed a limit. Then, the processing circuitry in the treatment planning apparatus 200 stores a treatment plan including a rotation speed corresponding to the state of the specified irradiation angle.

The radiation therapy apparatus 400 acquires the treatment plan including information of the rotation speed during the stop period of the radiation irradiation from the treatment planning apparatus 200, and performs radiation therapy along the acquired treatment plan. Note that the change function 435f in the radiation therapy apparatus 400 can monitor an actual administration dose when performing rotation irradiation along the acquired treatment plan, as in the first embodiment.

In the aforementioned embodiment, the case where the rotation speed during the irradiation period of the radiation is constant has been described; however, the control function 435a can also change the rotation speed during the irradiation period of the radiation. For example, the control function 435a continuously changes the rotation of the gantry so that the rotation speed at an intermediate time point in the irradiation period of the radiation is relatively high and the rotation speed at an intermediate time point in the stop period of the radiation is relatively low.

Figure 8:
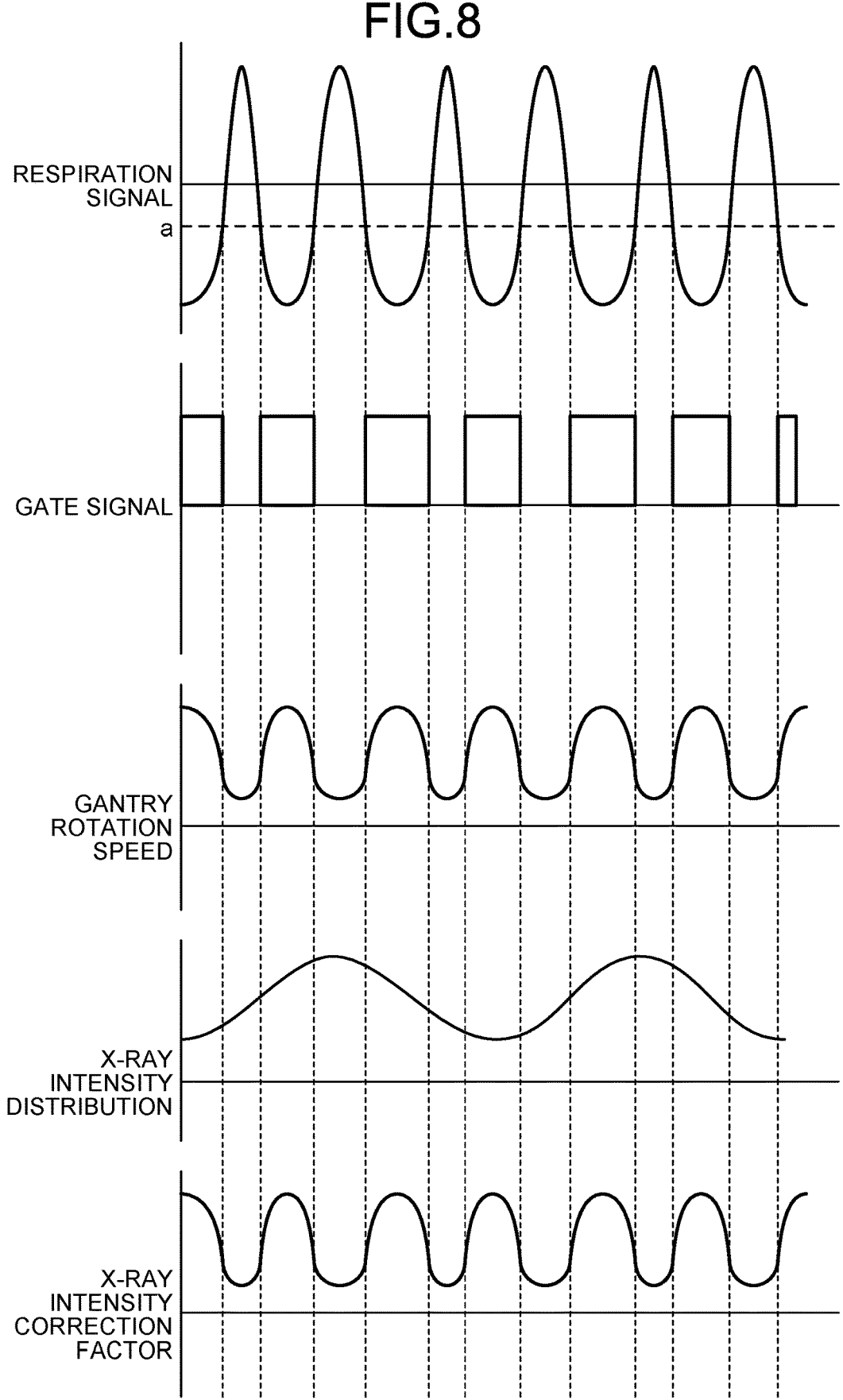
FIG. 8 is a diagram for explaining control by a control function according to the second embodiment.

FIG. 8 is a diagram for explaining control by the control function 435a according to the second embodiment. FIG. 8, the first stage indicates a respiration signal, the second stage indicates a gate signal, the third stage indicates the rotation speed of the gantry 410, the fourth stage indicates an X-ray intensity distribution, and the fifth stage indicates an X-ray intensity correction factor.

For example, the control function 435a compares the respiration signal illustrated in the first stage of FIG. 8 with the threshold "a" and transmits the gate signal to the gantry 410 in accordance with a respiratory phase below the threshold "a", thereby irradiating a respiratory phase corresponding to the gate signal with radiation. Moreover, the control function 435a continuously changes the rotation speed of the gantry 410 through the period during which the gate signal is transmitted and the radiation is applied and the period during which no radiation is applied, as illustrated in the third stage of FIG. 8.

Here, the control function 435a controls the rotation speed so that the gantry rotation speed is maximized at substantially the center of the gate signal. Note that since an actual central position of the gate signal is not able to be specified in real time, the control function 435a estimates the central position of the gate signal on the basis of a past gate signal (immediately previous gate signal or gate signal corresponding to the average respiration signal), and controls the rotation of the gantry 410 so that the rotation speed is maximized at the estimated central position. In this way, the control function 435a can reduce a load on the apparatus by continuously changing the rotation speed of the gantry 410, as compared with a case where the rotation speed is suddenly changed.

On the other hand, when the rotation speed is changed during radiation irradiation, it is conceivable that a dose deviates from a dose of a plan formulated assuming a constant speed. For example, the dose intensity of radiation in radiation therapy is determined for each time as illustrated in the fourth stage of FIG. 8. Consequently, when the rotation speed is changed during radiation irradiation showing such a change in dose distribution, a dose in a part where the rotation speed is low is administered higher than that in a part where the rotation speed is high, resulting in a deviation from the dose of the plan.

Therefore, the control function 435a changes the irradiation dose of radiation during the irradiation period of the radiation in accordance with the rotation speed. Specifically, when doses to a target to be irradiated with the radiation from a certain angle range are the same, the control function 435a increases the irradiation dose per unit time as the rotation speed is high, and decreases the irradiation dose per unit time as the rotation speed is low. For example, as illustrated in the fifth stage of FIG. 8, the control function 435a calculates a correction factor according to a change in the rotation speed, and performs control to generate, at each time, a radiation intensity in which the calculated correction factor and a dose intensity change are applied. That is, the control function 435a can administer the dose of the plan by calculating a correction factor indicating a change similar to a change in the rotation speed and applying the calculated correction factor to the dose intensity change.

The aforementioned embodiment can also be applied, for example, in combination with the formulation of a treatment plan by processing circuitry (not illustrated) in the treatment planning apparatus 200. For example, the processing circuitry in the treatment planning apparatus 200 performs the change function 435f described in the first embodiment and the predicted administration dose reaches the target dose; however, when a limit to an organ at risk is exceeded, the processing circuitry reduces the rotation speed during the stop period of radiation irradiation without changing the administration dose in the formulated treatment plan, and changes the treatment plan so that the rotation speed is continuously changed while allowing the irradiation angles of radiation to be dense.

Here, the processing circuitry in the treatment planning apparatus 200 calculates a correction factor showing a change similar to that in the rotation speed, and changes the treatment plan to generate, at each time, a radiation intensity in which the calculated correction factor and the formulated dose intensity change are applied.

The radiation therapy apparatus 400 acquires the treatment plan from the treatment planning apparatus 200, and performs radiation therapy along the acquired treatment plan. Note that the change function 435f in the radiation therapy apparatus 400 can monitor an actual administration dose when performing rotation irradiation along the acquired treatment plan, as in the first embodiment.

As described above, according to the second embodiment, the control function 435a changes the rotation speed of the gantry 410 in accordance with the irradiation period of radiation and the stop period of the radiation during the rotation of the gantry 410. Consequently, the radiation therapy apparatus 400 according to the second embodiment can change the state of the irradiation angle of the radiation, and reduce radiation exposure to an organ at risk without changing an administration dose.

Furthermore, according to the second embodiment, the control function 435a controls the rotation of the gantry 410 so that the rotation speed during the irradiation period of the radiation is relatively high and the rotation speed during the stop period of the radiation is relatively low. Consequently, the radiation therapy apparatus 400 according to the second embodiment can allow the irradiation angles of the radiation to be dense, and reduce radiation exposure to an organ at risk without changing an administration dose.

Furthermore, according to the second embodiment, the control function 435a continuously changes the rotation of the gantry so that the rotation speed at an intermediate time point in the irradiation period of the radiation is relatively high and the rotation speed at an intermediate time point in the stop period of the radiation is relatively low. Consequently, the radiation therapy apparatus 400 according to the second embodiment can prevent an increase in a load applied to the apparatus.

Furthermore, according to the second embodiment, the control function 435a changes the irradiation dose of radiation during the irradiation period of the radiation in accordance with the rotation speed. Consequently, the radiation therapy apparatus 400 according to the second embodiment can correct a deviation of an administration dose due to a change in the rotation speed.

Furthermore, according to the second embodiment, when doses to a target to be irradiated with the radiation from a certain angle range are the same, the control function 435a increases the irradiation dose per unit time as the rotation speed is high, and decreases the irradiation dose per unit time as the rotation speed is low. Consequently, the radiation therapy apparatus 400 according to the second embodiment can appropriately correct a deviation of an administration dose due to a change in the rotation speed.

Third Embodiment

In the third embodiment, a case where radiation irradiation is performed while rotating the gantry 410 multiple times will be described. Note that the radiation therapy apparatus 400 according to the third embodiment is different in control by the control function 435a as compared with the first embodiment. Hereinafter, this will be mainly described.

The control function 435a according to the third embodiment allows radiation to be applied while rotating the gantry 410 multiple times. Specifically, the control function 435a performs control so that radiation is applied at a different irradiation angle for each rotation while rotating the gantry 410 multiple times. Here, the control function 435a rotates the gantry 410 at a constant rotation speed in each rotation.

As described above, when the rotation speed of the gantry 410 is set to a constant speed, the irradiation angles are sparse. In order to administer a target dose in such a state, a dose rate needs to increase. However, when the dose rate is increased, a dose to a normal tissue in front of the irradiation direction relatively increases. Therefore, in the third embodiment, radiation is applied aiming at the sparse irradiation angles by multiple rotations, so that the target dose is stably secured without changing a dose rate.

For example, the control function 435a allows radiation to be applied while rotating the gantry in a first direction and a second direction opposite to the first direction. Then, the control function 435a controls the rotation of the gantry 410 so that an irradiation angle of the radiation in the second direction is different from that of the radiation in the first direction.

FIG. 9 is a diagram illustrating irradiation angles of radiation applied by the radiation therapy apparatus according to a third embodiment. In FIG. 9, the upper part indicates a case where the gantry 410 is rotated once in the first direction and radiation is applied in irradiation angles of regions R1. Furthermore, in FIG. 9, the lower part indicates a case where the gantry 410 is rotated once in the second direction (direction opposite to the first direction) and radiation is applied in irradiation angles of regions R2.

For example, as illustrated in the upper part of FIG. 9, the control function 435a allows radiation to be applied at the irradiation angles of the regions R1 on the basis of the gate signal while the gantry 410 in the first direction. Then, as illustrated in the lower part of FIG. 9, the control function 435a allows radiation to be applied at the irradiation angles of the regions R2 on the basis of the gate signal while the gantry 410 in the second direction. That is, the control function 435a controls the rotation irradiation in the second direction to be performed with respect to sparse open angles at which no radiation is applied in the rotation irradiation in the first direction.

Here, the control function 435a controls a timing at the start of rotation of the gantry 410 or a rotation speed immediately after the start of the rotation of the gantry 410, thereby allowing the irradiation angle of the radiation in the second direction to be different from that of the radiation in the first direction. That is, the control function 435a controls a rotation start timing or a rotation speed in the second direction so that a period during which the gate signal based on the respiration of the treatment subject is ON is near the center of the open angle.

The aforementioned embodiment can also be applied, for example, in combination with the formulation of a treatment plan by processing circuitry (not illustrated) in the treatment planning apparatus 200. For example, when the processing circuitry in the treatment planning apparatus 200 performs the change function 435f described in the first embodiment and the predicted administration dose does not reach the target dose, the predicted administration dose can be allowed to reach the target dose without increasing a dose rate by applying the present embodiment.

In such a case, the processing circuitry in the treatment planning apparatus 200 acquires the average respiration signal of the treatment subject at the time before treatment and calculates the length of the gate signal. Then, the processing circuitry in the treatment planning apparatus 200 calculates an administration dose when radiation is applied on the basis of a dose rate in the formulated treatment plan and the calculated length of the gate signal, and compares the calculated administration dose with the target dose. When the calculated administration dose is less than the target dose, the processing circuitry in the treatment planning apparatus 200 secures the target dose by performing rotation irradiation multiple times without changing the dose rate in the formulated treatment plan (or by lowering the dose rate).

The processing circuitry in the treatment planning apparatus 200 plans radiation irradiation with the aforementioned multiple rotations and stores a treatment plan including the planned radiation irradiation with the multiple rotations.

The radiation therapy apparatus 400 acquires the treatment plan including the radiation irradiation with the multiple rotations from the treatment planning apparatus 200, and performs radiation therapy along the acquired treatment plan. Note that the change function 435f in the radiation therapy apparatus 400 can monitor an actual administration dose when performing rotation irradiation along the acquired treatment plan, as in the first embodiment.

In the aforementioned embodiment, the case where radiation irradiation of multiple rotations is performed by rotating the gantry 410 in different directions has been described. However, embodiments are not limited thereto and radiation irradiation may also be performed while rotating the gantry 410 multiple times in the same direction.

As described above, according to the third embodiment, the control function 435a allows radiation to be applied while rotating the gantry 410 multiple times. Consequently, the radiation therapy apparatus 400 according to the third embodiment can increase the irradiation angle of the radiation, and stably secure an administration dose without increasing a dose to a normal tissue in front of an irradiation target.

Furthermore, according to the third embodiment, the control function 435a allows radiation to be applied while rotating the gantry in the first direction and the second direction opposite to the first direction. Consequently, the radiation therapy apparatus 400 according to the third embodiment can easily implement radiation irradiation of multiple rotations.

Furthermore, according to the third embodiment, the control function 435a controls a timing at the start of rotation of the gantry 410 or a rotation speed immediately after the start of the rotation of the gantry 410, thereby allowing the irradiation angle of the radiation in the second direction to be different from that of the radiation in the first direction. Consequently, the radiation therapy apparatus 400 according to the third embodiment can appropriately control an irradiation angle for each rotation.

Other Embodiments

In addition to the first to the third embodiments described above, other types of embodiments may also be carried out in different forms.

In the aforementioned embodiments, respective processing functions of the processing circuitry 435 have been described. For example, the aforementioned respective processing functions are stored in the memory 434 in the form of computer programs that can be executed by a computer. The processing circuitry 435 reads the computer programs from the memory 434 and executes the read computer programs, thereby performing processing functions corresponding to the executed computer programs. In other words, the processing circuitry 435 in the state where the computer programs are read has respective processing functions illustrated in FIG. 4.

Note that, in FIG. 4, an example in which respective processing functions are implemented by the single processing circuitry 435 has been described; however, embodiments are not limited thereto. For example, the processing circuitry 435 may be configured by combining a plurality of independent processors, and respective processors may implement respective processing functions by executing respective computer programs. Furthermore, respective processing functions of the processing circuitry 435 may be implemented by being appropriately distributed or integrated into a single or a plurality of processing circuits.

Furthermore, the term "processor" used in the aforementioned each embodiment, for example, means a circuit such as a central processing unit (CPU), a graphics processing unit (GPU), an application specific integrated circuit (ASIC), a programmable logic device (for example, a simple programmable logic device (SPLD)), a complex programmable logic device (CPLD), and a field programmable gate array (FPGA). Instead of storing the computer programs in the storage circuit, the computer programs may be directly incorporated in the circuit of the processor. In such a case, the processor performs the functions by reading and executing the computer programs incorporated in the circuit. Furthermore, each processor of the present embodiment is not limited to being configured as a single circuit for each processor, and one processor may be configured by combining a plurality of independent circuits to perform the functions thereof.

The computer program executed by the processor is provided by being incorporated in advance in a read only memory (ROM), a storage unit, and the like. Note that the computer program may be provided by being stored on a computer readable storage medium, such as a CD (compact disc)-ROM, a flexible disk (FD), a CD-R (recordable), and a digital versatile disc (DVD), in a file format installable or executable in these devices. Furthermore, the computer program may be provided or distributed by being stored on a computer connected to a network such as the Internet and downloaded via the network. For example, the computer program is configured as a module including each functional unit. As actual hardware, the CPU reads and executes the computer program from the storage medium such as a ROM, so that each module is loaded on a main storage device and generated on the main storage device.

According to at least one embodiment described above, an administration dose can be stably secured while preventing an increase in radiation exposure to a normal tissue.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation therapy apparatus that allows radiation to be applied while rotating a gantry and controls irradiation and stopping of the radiation during rotation of the gantry based on a respiration of a treatment subject, the radiation therapy apparatus comprising:
processing circuitry configured to
detect the respiration of the treatment subject,
determine, based on the detected respiration of the treatment subject detected before irradiation of the radiation, a respiratory phase range in which the radiation will be applied in the respiration of the treatment subject,
predict an administration dose based on the determined respiratory phase range, and change at least one of a dose rate of the radiation to be applied to the treatment subject and a rotation speed of the gantry so that the predicted administration dose reaches a target dose, and
perform control according to the change with respect to the at least one of the dose rate of the radiation and the rotation speed of the gantry.

2. The radiation therapy apparatus according to the claim 1, wherein the processing circuitry is further configured to
identify average respiration information based on the detected respiration of the treatment subject
determine the respiratory phase range based on the identified average respiration information.

3. The radiation therapy apparatus according to the claim 1, wherein the processing circuitry is further configured to change the at least one of the dose rate of the radiation and the rotation speed of the gantry based on a comparison result between the predicted administration dose of the radiation applied in the determined respiratory phase range and a planned dose during the rotation of the gantry.

4. The radiation therapy apparatus according to the claim 1, wherein the processing circuitry is further configured to calculate a difference between the predicted administration dose of the radiation applied in the determined respiratory phase range and a planned dose, and change the dose rate of the radiation to be applied to the treatment subject so that the calculated difference is reduced during the rotation of the gantry.

5. The radiation therapy apparatus according to the claim 1, wherein the processing circuitry is further configured to change the rotation speed of the gantry in accordance with an irradiation period of radiation and a stop period of the radiation during the rotation of the gantry.

6. The radiation therapy apparatus according to the claim 5, wherein the processing circuitry is further configured to control the rotation of the gantry so that the rotation speed during the irradiation period of the radiation is relatively high and the rotation speed during the stop period of the radiation is relatively low.

7. The radiation therapy apparatus according to the claim 6, wherein the processing circuitry is further configured to continuously change the rotation of the gantry so that the rotation speed at an intermediate time point during the irradiation period of the radiation is relatively high and the rotation speed at an intermediate time point during the stop period of the radiation is relatively low.

8. The radiation therapy apparatus according to the claim 7, wherein the processing circuitry is further configured to change an irradiation dose of the radiation during the irradiation period of the radiation in accordance with the rotation speed.

9. The radiation therapy apparatus according to the claim 8, wherein, when doses to a target to be irradiated with the radiation from a certain angle range are identical, the processing circuitry is further configured to increase an irradiation dose per unit time when the rotation speed is high, and decrease the irradiation dose per unit time when the rotation speed is low.

10. The radiation therapy apparatus according to the claim 1, wherein the processing circuitry is further configured to allow the radiation to be applied while rotating the gantry multiple times.

11. The radiation therapy apparatus according to the claim 10, wherein the processing circuitry is further configured to allow radiation to be applied while rotating the gantry in a first direction and a second direction opposite to the first direction.

12. The radiation therapy apparatus according to the claim 11, wherein the processing circuitry is further configured to control the rotation of the gantry so that an irradiation angle of the radiation in the second direction is different from an irradiation angle of the radiation in the first direction.

13. The radiation therapy apparatus according to the claim 12, wherein the processing circuitry is further configured to control a timing at a start of rotation of the gantry or a rotation speed immediately after the start of the rotation of the gantry, to allow the irradiation angle of the radiation in the second direction to be different from the irradiation angle of the radiation in the first direction.

14. A radiation therapy method performed by a radiation therapy apparatus that allows radiation to be applied while rotating a gantry and controls irradiation and stopping of the radiation during rotation of the gantry based on a respiration of a treatment subject, the radiation therapy method comprising:
detecting the respiration of the treatment subject;
determining, based on the detected respiration of the treatment subject detected before irradiation of the radiation, a respiratory phase range in which the radiation will be applied in the respiration of the treatment subject;
predicting an administration dose based on the determined respiratory phase range, and changing at least one or both of a dose rate of the radiation to be applied to the treatment subject and a rotation speed of the gantry so that the predicted administration dose reaches a target dose; and
performing control according to the change with respect to the at least one of the dose rate of the radiation and the rotation speed of the gantry.

* * * * *